United States Patent [19]

Ruff

[11] Patent Number: 4,716,906
[45] Date of Patent: Jan. 5, 1988

[54] BLOOD PRESSURE CUFF

[75] Inventor: Gray E. Ruff, Hillsboro, Oreg.

[73] Assignee: SpaceLabs, Inc., Bothell, Wash.

[21] Appl. No.: 880,249

[22] Filed: Jun. 30, 1986

[51] Int. Cl.⁴ .............................................. A61B 5/02
[52] U.S. Cl. ................................. 128/686; 128/327;
128/677
[58] Field of Search ............... 128/672, 677, 686, 327,
128/402–403

[56] References Cited

U.S. PATENT DOCUMENTS

| | | | |
|---|---|---|---|
| 3,654,931 | 4/1972 | Hazlewood | 128/327 |
| 3,659,592 | 5/1972 | Natkanski | 128/686 |
| 3,669,096 | 6/1972 | Hurwitz | 128/686 |
| 3,752,148 | 8/1973 | Schmalzbach | 128/686 |
| 4,353,374 | 10/1982 | Rebbe et al. | 128/686 |
| 4,354,503 | 10/1982 | Golden | 128/686 |
| 4,429,699 | 2/1984 | Hatschek | 128/681 |
| 4,465,076 | 8/1984 | Sturgeon | 128/686 |
| 4,527,566 | 7/1985 | Abare | 128/402 |
| 4,548,249 | 10/1985 | Slaughterbeck | 128/686 X |

FOREIGN PATENT DOCUMENTS 0949352 6/1974 Canada ............................ 128/686
2220233 5/1978 Fed. Rep. of Germany ...... 128/686

Primary Examiner—William E. Kamm
Assistant Examiner—Angela D. Sykes
Attorney, Agent, or Firm—Seed and Berry

[57] ABSTRACT

A blood pressure cuff particularly for use with ambulatory blood pressure products and suitable for use on either the left or right limbs of the patient is disclosed. The cuff includes an elongated, flexible band having a body side face and an outward face and a compartment. It further includes an inflatable bladder having a centerline and adapted for placement within the compartment in either a first position or a second position rotated 180° from the first position. The bladder includes a portion coupled on one side of the centerline and adapted to protrude through an opening in the band when the bladder is in either the first or second position. The opening comprises two separate openings on either side of the centerline. First and second indicia placed adjacent the openings on the outward face of the band identify the position of the protruding portion for use on either the left or right side limb.

6 Claims, 4 Drawing Figures

BLOOD PRESSURE CUFF

BACKGROUND OF THE INVENTION

The present invention relates to blood pressure cuffs used for taking blood pressure measurements, more particularly, to cuffs used with the limbs of human patients.

Blood pressure cuffs are well known in the prior art and comprise an elongated flexible band having a predetermined length and width, a body side face and a outward face. The band is adapted to be wrapped around a limb, such as an arm or leg, to measure blood pressure. Attachment means such as VELCRO TM is provided with the band to hold the band on the limb.

The front and back faces of the band are joined together around their peripheries to form a compartment into which an inflatable bladder is inserted. A hose portion coupled to the bladder and usually integrally formed therewith extend out from the compartment through an opening in the periphery.

When wrapping the band around the arm, it is desirable for accuracy of measurement that the center of the bladder be located over the brachial artery on the inner side of the upper arm. It has been found most convenient in ambulatory measurement applications when wrapping the band around the arm that the hose portion extend through a top periphery or edge of the cuff such that a hose coupled between the cuff and monitoring device is then routed up the front of the arm across the back of the neck to the other side of the body to the monitoring device which is usually strapped to the patient's waist. In order to accomplish this the slot in the periphery of the cuff is offset from the center of the bladder and located solely on one side thereof so that the hose portion of the bladder extends along the front of the arm. Prior art cuffs of which the inventor is aware have only a single opening offset as described above. If the cuff is designed for use on the left arm, the hose portion and coupling hose will be inconveniently located under the patient's armpit when the cuff is used on the right arm and vice versa. It is desirable therefore to provide a single cuff design which is suitable for use on either arm.

SUMMARY OF THE INVENTION

The present invention relates to a blood pressure cuff adapted for use on a limb of a patient on either the left or right side of the body. It comprises a band having a body side face and an outward face and a compartment. The compartment is open to ambient atmosphere through at least a pair of openings in the band. The cuff further includes an inflatable bladder having a centerline, the bladder adapted to be removably confined within said compartment in either a first position or a second position rotated 180° from the first position. The bladder includes a portion which protrudes from the compartment through one of the openings, the protruding portion coupled to the bladder spaced apart from the centerline.

In the preferred embodiment, the openings comprise a pair of openings spaced apart from one another on either side of the centerline and formed at the periphery of the two faces of the band where the faces are joined together. The protruding portion extends through a first opening of the pair when the bladder is in the first position and a second opening when the bladder is in the second position. First and second indicia are placed on the outward face adjacent the first and second openings, respectively, to identify which is to be used for right and left side limbs.

In ambulatory blood pressure monitoring applications, the openings are formed on the top periphery of the band with indicia to identify right arm and left arm placed nearby. A third indicia identifying the centerline of the bladder for placement along the brachial artery is also provided on the outward face of the band.

The cuff further includes hook-like fastener material on an area of the body side face near one end of the band with loop-like fastener material on an area of the outward face at the opposite end.

DETAILED DESCRIPTION OF THE DRAWINGS

Figure 1:
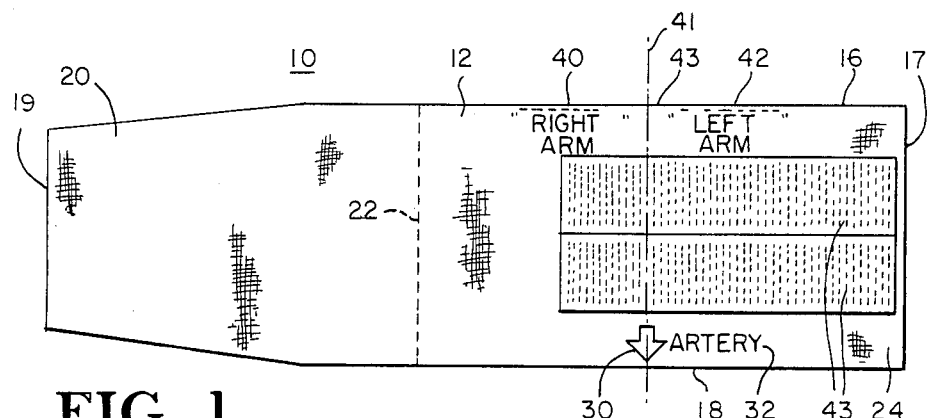
FIG. 1 is an outside planar elevational view of the band portion of the preferred embodiment blood pressure cuff of the present invention.
Figure 1A:
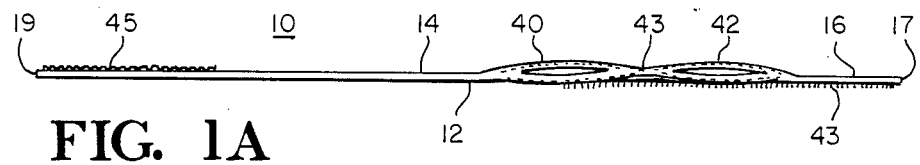
FIG. 1A is a top view of the band portion of FIG. 1.
Figure 2:
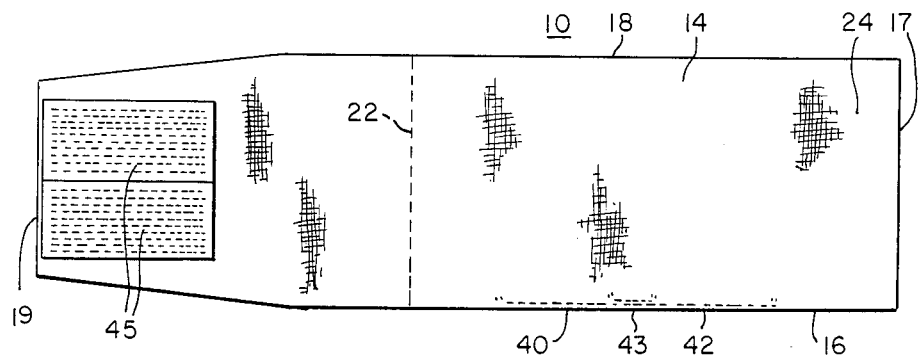
FIG. 2 is a body side planar elevational view of the band portion of the cuff of FIG. 1.
Figure 3:
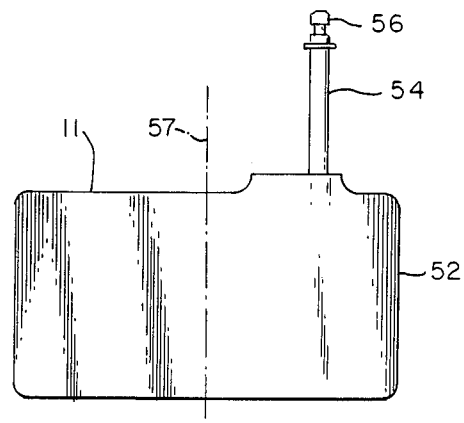
FIG. 3 is a planar elevational view of an inflatable bladder portion of the cuff for use with th band portion of FIGS. 1 and 2.

Referring now to the FIGS., there is shown a blood pressure cuff comprising an elongated flexible band designated generally 10 having an overall length L with width W along most of its length. The cuff further includes the inflatable bladder 11 in FIG. 3. The band comprises an outward face 12 in FIG. 1 and a body-side face 14 in FIG. 2 which are coupled together along their common periphery formed by top edge 16, end edge 17, bottom edge 18 and opposite end edge 19. The faces may be made of any suitable fabric or material such as nylon or a polyester cotton blend. In the preferred embodiment, the faces are sewn together along their peripheries.

One end 20 of the band 10 narrows in width to form edge 19 and creates a taper which makes the cuff easier to handle when wrapping it around a patient's limb. The two faces are sewn together across their width along dotted line 22 at a location near the center but closer to the tapered end. This creates a compartment in the band opposite the tapered end, the compartment formed by dotted line 22, top edge 16, end edge 17, and bottom edge 18 and the two faces 12 and 14.

An arrow 30 with the word ARTERY 32 adjacent thereto is printed or placed on the outward face 12 of the band 10 with arrow 30 pointing to and adjacent the bottom edge 18. The point of the arrow 30 points to a spot near the halfway point between end edge 17 and dotted line 22 but closer to the dotted line 22 than end edge 17.

Two equally sized openings 40 and 42 are provided between the two faces along top edge 16 such that the faces 12 and 14 can be spread apart at the openings to gain access to the interior of compartment 28. The openings are separated by a short distance and are symmetrically placed on the left and right sides of an imaginary line 41 which runs across the width of the band, perpendicular to the top and bottom edges 16 and 18 and lying coaxially with the centerline of arrow 30.

Just below the slot 42 which is nearest end edge 17, the words LEFT ARM are printed or placed on the outward face 12 of the band while the words RIGHT ARM are printed or placed on face 12 below the slot 40 nearest dotted line 22.

In the preferred embodiment a band suitable for use on adults is 20.25 inches long and a maximum of 5.80 inches wide tapering at edge 19 to 4.25 inches. The dotted line 22 is parallel to and spaced apart by 11.50 inches from end edge 17. The imaginary line 41 coaxial with arrow 30 is 6.0 inches from end edge 17, and each slot 40 and 42 is 2.5 inches long their facing ends being 1.0 inches apart.

The outward face 12 of the band is provided with a rectangularly shaped region of loop fastener material 43 usually made of nylon. A suitable material is that which is sold under the trademark VELCRO TM. In the preferred embodiment a 12 to 18 per inch zig-zag stitch is used. The loop material covers an area 4 inches wide by 8 inches long starting near the end edge 17 and running lengthwise along the face 12. A mating-hook portion of fastener material 45, covering an area of 4 inches by 4 inches, is provided on the body-side face 14 starting near edge 19.

The bladder 11 is made from an inflatable rubber material and comprises a main chamber portion 52 and an integrally formed hose 54 with a barbed nipple connector 56 at its distal end, the hose open to the interior of chamber portion 52 where it joins therewith. In the preferred embodiment the bladder is 4.9 inches wide and 10.25 inches long with the hose located 3.75 inches from one end.

The bladder is foldable and can be inserted into and removed from the compartment of the band through either of openings 40 or 42. When positioned within the compartment the centerline of the bladder 57 lies roughly along the imaginary line separating the slots 40 and 42 coaxial with arrow 30 and the hose will extend out of the compartment through either opening 40 or 42.

When in use the bladder is placed within the compartment with the hose extending out from one of the openings 40 or 42 depending on the arm to be used. With face 14 disposed to engage the arm, the band is positioned between the patient's arm and chest wall so that the arrow lies along the brachial artery on the inside of the arm. The band is wrapped around the arm and the hook material of face 14 is pressed against the loop material on face 12 to hold the cuff in place. On a larger arm there will be less overlap and some portion of the loop material will extend beyond the leading edge of the hook material and possibly come in contact with the patient's clothing. To avoid annoying interference between the fastener material and the patient's clothing the loop material is placed on the outwardly facing side 12.

If the cuff is wrapped around the left arm, the hose should extend through the slot 42 marked LEFT ARM. This will insure that when the arrow 30 points to the brachial artery, the hose coupled to the barb will extend upwardly along the front of the patient's arm and avoid the armpit. If the cuff is to be wrapped around the right arm, the bladder should be removed through slot 42, turned around 180 degrees and inserted into the compartment through opening 40 with the hose 54 extending out from the cuff now through opening 40 marked RIGHT ARM. Then when the cuff is wrapped around the right arm with the arrow 30 pointing to the brachial artery, the hose coupled to the cuff will extend upwardly along the front of the right arm and not along the inside of the arm into the armpit.

What is claimed is:

1. A blood pressure cuff adapted to be positioned on a limb of a body comprising:
    an elongated flexible band having first and second ends, said band having a body side ace intended for engagement with the limb and an outward face, said band having a compartment therein which is partially open to ambient atmosphere through a pair of openings in said band;
    an inflatable bladder having a centerline, said bladder being removably confined within said compartment in either a first position or a second position rotated 180° from said first position with the centerline substantially aligned with an artery in said limb in either said first or second position when said band is properly positioned on said limb, said bladder having a portion protruding out from said compartment through one of said pair of openings which are spaced apart from one another on either side of said centerline, said protruding portion protruding through a first one of said openings when said bladder is in said first positin and a second one of said openings when said bladder is in said second position.

2. The blood pressure cuff of claim 1 wherein said body side and outward faces are joined together at their peripheries except at said pair of openings to form said compartment; and
    said cuff further commmprises first and second indicia placed on said outward face adjacent said first and second openings, respectively to identifying which of said bladder positions should be used for said left side and right side limbs.

3. The blood pressure cuff of claim 2 wherein said cuff further comprises third indicia on said outward face, said indicia indicating the approximate location of said centerline of said bladder confined within said compartment for aligning said centerline in the proper position on said limb.

4. The blood pressure cuff of claim 3 wherein said blood pressure cuff is adapted for use on the arm of said patient with an ambulatory blood pressure monitor and said pair of openings and first and second indicia are located at the top periphery of said band and said first and second indicia identify the right and left arm, respectively.

5. The blood pressure cuff of claim 4 wherein said third indicia refers to the brachial artery of the arm.

6. The blood pressure cuff of claim 1 wherein said compartment is formed adjacent said first end of said band and said cuff further comprises:
    hook-like fastener material on an area of said body side face adjacent said second end and loop-like fastener material on an area of said outward face adjacent said first end for mating engagement with said hook-like fastener material.

* * * * *

UNITED STATES PATENT AND TRADEMARK OFFICE
CERTIFICATE OF CORRECTION

PATENT NO. : 4,716,906
DATED : January 5, 1988
INVENTOR(S) : Gray E. Ruff

It is certified that error appears in the above—identified patent and that said Letters Patent is hereby corrected as shown below:

Claim 1, line 4, delete "ace" and substitute therefor --face--.

Claim 2, line 5, delete "commprises" and substitute therefor --comprises--.

Claim 2, line 7, delete the word "to".

Signed and Sealed this

Twenty-fourth Day of May, 1988

Attest:

DONALD J. QUIGG

Attesting Officer

Commissioner of Patents and Trademarks